United States Patent [19]
Eckenhoff et al.

[11] 3,987,790
[45] Oct. 26, 1976

[54] OSMOTICALLY DRIVEN FLUID DISPENSER

[75] Inventors: James Benjamin Eckenhoff, Palo Alto; Neil Arthur Johnson; Su Il Yum, both of Sunnyvale, all of Calif.

[73] Assignee: Alza Corporation, Palo Alto, Calif.

[22] Filed: Oct. 1, 1975

[21] Appl. No.: 618,492

[52] U.S. Cl. ............................. 128/260; 128/130; 128/172; 128/271; 128/213
[51] Int. Cl.² ........................................ A61M 31/00
[58] Field of Search ............ 128/260, 213, 127–131, 128/261, 271, 130, 172; 222/386.5, 389, 193; 206/.5

[56] References Cited
UNITED STATES PATENTS

| | | | |
|---|---|---|---|
| 3,604,417 | 9/1971 | Stolzenberg | 128/213 |
| 3,760,804 | 9/1973 | Higuchi | 128/260 |
| 3,760,984 | 9/1973 | Theeuwes | 128/260 X |
| 3,845,770 | 11/1974 | Theeuwes | 128/260 |
| 3,929,132 | 12/1975 | Higuchi | 128/260 |

FOREIGN PATENTS OR APPLICATIONS

| | | | |
|---|---|---|---|
| 949,513 | 6/1974 | Canada | 128/260 |

Primary Examiner—Aldrich F. Medbery
Attorney, Agent, or Firm—Thomas E. Ciotti; Paul L. Sabatine; Edward L. Mandell

[57] ABSTRACT

An osmotically driven fluid dispenser that is capable of being miniaturized and used as an implant to administer fluid drug compositions to animals and humans. The dispenser comprises a flexible inner bag adapted to contain the drug composition, a fluid tight plug fitted into the bag opening, a port in the plug through which the composition may be charged to the bag, an intermediate layer of an osmotically effective solute composition partly covering the bag exterior such that a band of the bag exterior proximate to the plugged end is not covered by the layer, an outer shape-retaining semipermeable membrane covering the layer of solute and forming a fluid tight seal at said band, and a tube that fits snugly through the port in the plug and extends substantially into the interior of the bag after the drug composition is charged to the bag, said tube providing an outlet through which the drug composition may be dispensed.

17 Claims, 4 Drawing Figures

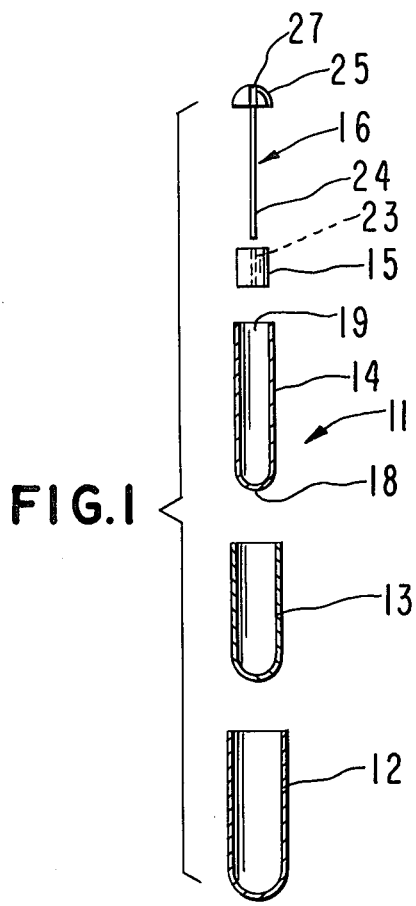
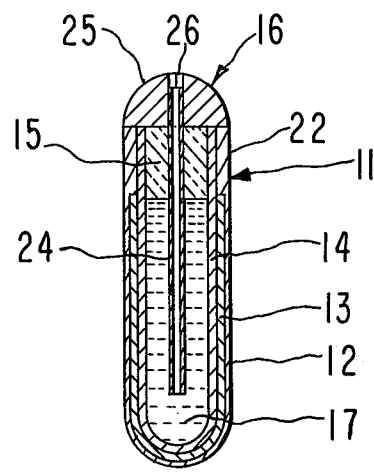
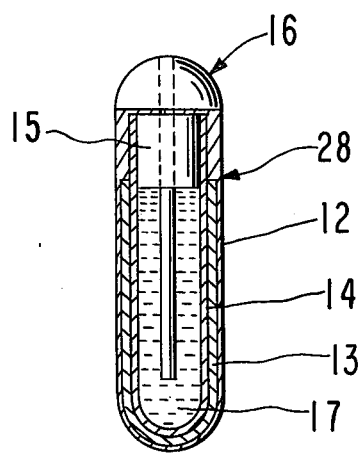
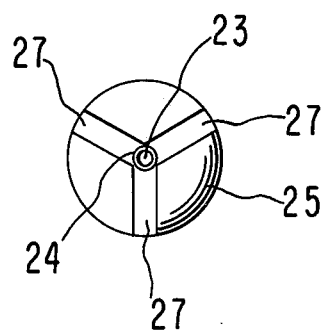

OSMOTICALLY DRIVEN FLUID DISPENSER

BACKGROUND OF THE INVENTION

1. Field of the Invention

The invention relates to improvements and modifications of an osmotically driven fluid dispenser.

2. Description of the Prior Art

The invention is an improvement in the osmotically driven dispensers described in commonly owned U.S. Pat. No. 3,760,984 and Canadian Pat. No. 949,513 (corresponds to U.S. Ser. No. 291,686 filed 25 Sept. 1972). Therefore these patents are believed to be relevant prior art, with the dispenser referred to in Canadian Pat. No. 949,513 as the "minipump" being especially relevant. The minipump is an osmotically driven dispenser whose size makes it especially useful as a therapeutic system for administering drugs to animals and humans. Its basic components are an inner flexible bag that holds the drug charge, an intermediate layer of an osmotically effective solute composition, such as an inorganic salt, that encapsulates the bag, an outer shape-retaining membrane that is permeable to water and that encapsulates both the layer of osmotically effective solute composition and the bag, and a filling-/discharge port that communicates with the interior of the bag.

In operation the bag is filled with drug via the filling-/discharge port and placed in an aqueous environment, such as a body cavity or within body tissue. Water is imbibed from the environment by the osmotically effective solute through the membrane into the space between the inner flexible bag and the membrane. Since the bag is flexible and the membrane is rigid, the imbibed water squeezes the bag inwardly thereby displacing drug out the filling/discharge port.

Minipumps of the above described structure and operation perform well but are not beyond being improved. Two shortcomings of those dispensers are, (1) they tend to lose drug in bulk through the filling/discharge port, especially when the dispenser is placed in an environment that experiences significant movement, and (2) air bubbles trapped in the bag during filling tend to completely or partially plug the filling/discharge port. The former shortcoming affects the constancy of the dosage rate adversely and may cause overdosing. The latter shortcoming may temporarily stop the dispensing or cause the dosage rate to be erratic or unpredictable. The present invention is directed towards eliminating or reducing both of these shortcomings.

SUMMARY OF THE INVENTION

One aspect of the invention is an improvement in an osmotically driven fluid dispenser. The dispenser comprises an inner flexible bag adapted to contain the fluid, an intermediate layer of an osmotically effective solute at least partly encapsulating the bag, an outer shape-retaining membrance encapsulating the layer of osmotically effective solute, said membrane being at least in part permeable to water, and a port that extends from the interior of the flexible bag to the exterior of the dispenser through which the fluid may be charged into the bag and dispensed from the bag. The improvement in the above defined dispenser is a fluid flow moderator comprising a conduit that is adapted to fit snugly through said port and extend substantially into the interior of the bag after fluid has been charged into the bag.

Another aspect of the invention is an osmotically driven fluid dispenser of novel structure. This dispenser comprises an elongated flexible inner bag closed at one end and open at the other end and adapted to contain the fluid, a fluid tight plug fitted into the open end of the bag, a port in the plug that provides a passageway from the interior of the bag to the exterior of the dispenser through which the fluid may be charged into the bag, an intermediate layer of an osmotically effective solute composition partly covering the exterior of the bag such that a band of the bag exterior proximate to the open end of the bag is not covered by the layer, an outer shape-retaining semipermeable membrane covering the intermediate layer of osmotically effective solute composition and forming a fluid tight seal with the exterior of the bag at said band, and a conduit that is adapted to fit snugly through the port and extend substantially into the interior of the bag after the fluid is charged to the bag to provide an outlet through which fluid may be dispensed from the bag under pressure.

BRIEF DESCRIPTION OF THE DRAWINGS

In the drawings:

FIG. 1 is an elevational, exploded, partly sectional view of one embodiment of the dispenser of the invention;

FIG. 2 is an enlarged, sectional view of the dispenser of FIG. 1;

FIG. 3 is an enlarged, elevational, partly sectional view of another embodiment of thedispenserofthe invention; and FIG. 4 is an enlarged, top plan view of the flow moderator of the dispenser of FIG. 1.

Like numerals refer to like parts in the various figures.

DETAILED DESCRIPTION OF THE INVENTION

FIGS. 1 and 2 illustrate an osmotically driven fluid dispenser, generally designated 11. The basic components of dispenser 11 are an outer, shape-retaining, semipermeable membrane 12, an intermediate layer 13 of an osmotically effective solute, an inner flexible bag 14, a plug 15, and a flow moderator, generally designated 16.

Bag 14 is adapted to contain a fluid composition, such as an active agent composition 17 (FIG. 2) in fluid form. The term "active agent" as used herein means any compound or mixture of compounds that can be dispensed to produce a predetermined beneficial and useful result. Active agents include pesticides, germicides, biocides, algicides, rodenticides, fungicides, insecticides, antioxidants, plant growth promoters, plant growth inhibitors, preservating agents, surfactants, disinfectants, sterilization agents, catalysts, chemical reactants, fermentation agents, cosmetics, foods, nutrients, food supplements, drugs, vitamins, sex sterilants, fertility inhibitors, fertility promotors, air purifiers, microorganism attenuators, and other compositions that benefit the environment, surroundings, and habitat including animals and humans. In the preferred embodiment the active agent is a drug that produces a local or systemic physiologic or pharmacologic response when administered to animals or humans.

In order to be a suitable container for the fluid, the bag should be substantially impermeable to the composition and be compatible with the composition. By "compatible", it is meant that the bag should not be corroded, solubilized, or otherwise affected deleteriously by the composition. Additionally, when the composition is a drug or the like, the composition should not be significantly contaminated by the bag, such as by the extraction of leachables from the material forming the bag. Bag 14 may be made from elastomeric compositions that may be formed into thin sheets. The elastomeric properties of the bag composition and the thickness of the bag wall should be such as to cause the bag to readily collapse inwardly when a force is applied to the bag exterior. Such elastomeric compositions are disclosed in commonly owned U.S. Pat. No. 3,760,984 at col. 5, line 40 to col. 7, line 37 and in commonly owned Canadian Pat. No. 949,513 at p. 10, line 28 to p. 11, line 7, which disclosures are incorporated herein by reference.

Bag 14 is elongated and generally cylindrical and is closed at its end 18 and open at its opposite end 19. As seen in FIG. 2, bag 14 is partly encapsulated by the layer 13 of an osmotically effective solute composition such that a band 22 of the exterior of bag 14 proximate to open end 19 is not covered by layer 13. The purpose of layer 13 is to imbibe water across membrane 12 into the space between the exterior of bag 14 and the inner surface of membrane 12, that is, the space occupied by layer 13. Osmotically effective solute compositions that may be used to form layer 13 are disclosed in said U.S. Pat. No. 3,760,984 at col. 7, line 38 to col. 8, line 2 and in said Canadian Pat. No. 949,513 at p. 18, lines 22–27, which disclosures are incorporated herein by reference.

Solute layer 13 is in turn encapsulated by outer membrane 12. Membrane 12 also covers band 22 and forms a fluid tight seal therewith. At least a part of membrane 12 is permeable to water. Preferably all of membrane 12 is permeable to water. Membrane 12 is impermeable to the osmotically effective solute composition. Membrane 12 is also shape-retaining, that is, it is sufficiently rigid to be substantially undeformed by the hydrostatic pressure that is generated in the space between its inner surface and the exterior of bag 14 by the water imbibed by layer 13. The thickness and composition of membrane 12 affects the rate at which water will be imbibed through it by solute layer 13. Such membranes and compositions that may be used to form them are disclosed in said U.S. Pat. No. 3,760,984 at col. 4, line 53 to col. 5, line 39 and in said Canadian Pat. No. 949,513 at p. 9, line 24 to p. 10, line 27, which disclosures are incorporated herein by reference.

Plug 15 fits into the open end 19 of bag 14. Plug 15 is generally cylindrical and is approximately as long as band 22. The exterior of plug 15 forms a fluid tight seal with the portion of the interior surface of bag 14 with which it is in contact. Plug 14 has an axial, central bore 23 extending completely through it. Bore 23 provides access to the interior of bag 14 for filling bag 14 with composition agent 17. Bore 23 is also adapted to receive flow moderator 16. Plug 15 may be made from the same materials as are used to make flexible bag 14; however, the dimensions of plug 15 should be such that it is subtantially inflexible.

Flow moderator 16 provides the passageway from the interior of bag 14 to the exterior of dispenser 11 by which composition 17 is discharged from dispenser 11. Flow moderator 16 comprises a conduit, in the form of a rigid cylindrical tube 24, and a head or cap 25. Tube 24 and head 25 may be made from suitable plastics or metals, respectively. The outer diameter of tube 24 is approximately the same as the diameter of bore 23 such that tube 24 may be inserted through bore 23 into bag 14 with tube 24 fitting snugly within bore 23 so as to form an essentially fluid tight seal with plug 15. The length of tube 24 is such that it extends into bag 14 to at least about 50% of the elongated dimension of the interior of bag 14, i.e., the distance from the inner side of end 18 to the inner end of plug 15. Preferably tube 24 extends into bag 14 over substantially the entire, but not all of (say 85% to 95%), of said elongated dimension. The inner diameter of tube 24 is correlated to the length of tube 24 such that substantial diffusional flow of composition 17 through tube 24 will not occur. Tube 24 is, in effect, a capillary that provides resistance to the flow of composition 17, thereby reducing or eliminating bulk loss of composition 17 from the outlet port of dispenser 11. Although not shown in the drawings, tube 24 may extend outwardly from the exterior of head 25 to provide a site for attachment of a catheter or other dispensing means. Head 25 is hemispherical and has a diameter approximately equal to the outer diameter of dispenser 11. It also has a diametrical bore 26 for receiving tube 24. As seen in FIG. 2, the flat side of head 25 fits against the top of plug 15 and the top edge of bag 14. Thus the spherical surface of head 25 provides a smooth blunt surface that generally aligns with the exterior surface of the bag-solute layer-membrane assembly, which bluntness and alignment are important if the dispenser is to be used as an implant to administer drugs to animals or humans. Referring to FIG. 4, head 25 has three radial, equispaced grooves 27 in its spherical surface that intersect at bore 26. The outer end of tube 24 is inset slightly from the spherical surface of head 25 (FIG. 2) and thus grooves 27 serve as flow channels for composition 17 exiting from the outer end of tube 24.

FIG. 3 illustrates an osmotic dispenser, generally designated 28 that is identical to dispenser 11 except in one respect, namely outer membrane 12 encapsulates the top edge of bag 14 and the top of plug 15 as well as the arcuate surfaces of layer 13 and band 22. As discussed below, this difference is caused by a difference in the techniques by which the membrane 12 is applied to dispensers 11 and 28. Like dispenser 11, dispenser 28 also consists of an outer, shape-retaining, semipermeable membrane 12, an intermediate layer 13 of an osmotically effective solute, an inner flexible bag 14 adapted to contain a fluid 17, a plug 15, and a flow moderator 16. These components are of identical structure, composition, and interelationship as their like numbered counterparts of dispenser 11 except for the single difference mentioned above.

The components of dispenser 11 may be made and assembled as follows. Bag 14 may be injection molded from suitable polymer compositions by known techniques. Bag 14 is then placed on a support means, such as a mandrel, and a suspension of the osmotically effective solute in an appropriate suspending medium is prepared. The supported bag 14 is then dipped repeatedly in the suspension to the desired depth, with intervening drying periods, until a layer 13 of desired thickness is formed. A solution of membrane material is then made and the supported, solute coated bag 14 is dipped repeatedly into the solution to a depth just above the top edge of bag 14, with intervening drying periods, until a membrane 12 of desired thickness is formed. The mandrel is then removed and plug 15, which may be injection molded by known techniques, is glued into the open end of bag 14. Head 25 may be machined by known techniques if it is metal, or injection molded by known techniques if made from a synthetic polymer. The end of tube 24 may be affixed within bore 26 by press-fitting, gluing, or other known techniques.

Dispenser 28 may be assembled as follows. A solute coated bag 14 is made as in the case of dispenser 11. Plug 15 is then fixed in place in the open end of bag 14 as in the case of dispenser 11. Membrane 12 of dispenser 28 is then applied to the solute coated, plugged bag 14 by air suspension-solution coating techniques in a Wurster coating apparatus. Such apparatus and techniques are well known. This manner of forming membrane 12 encapsulates the entire bag-solute layer-plug assembly. Accordingly, a hole must be formed through membrane 12 to bore 23 of plug 15. This may be done by drilling, punching, or equivalent techniques.

Dispensers 11 and 28 may be filled with fluid 17 via bore 23 of plug 15. For instance, the needle of a fluid loaded syringe may be inserted through bore 23 and the syringe's contents discharged into bag 14. To insure that a predetermined fluid pumping rate is achieved, it is desirable to completely fill bag 14 with fluid 17. After the bag is filled, tube 24 of flow moderator 16 is inserted through bore 23 to the position shown in FIGS. 2 and 3. As described above tube 24 functions as a capillary and inhibits loss of fluid 17 from the dispensers even though they are subjected to substantial movement or tipped upside down.

Dispensers 11 and 28 operate in the following manner. Once placed in an aqueous environment, such as within a body cavity or within body tissue, water from the environment is imbibed by layer 13 through membrane 12 at a rate determined by the osmotic activity of the osmotically effective solute, and the osmotic reflection coefficient, composition, thickness, and area of membrane 12. The imbibed water causes the volume of the space between the inner surface of membrane 12 and the exterior of bag 14 (the space initially occupied by layer 13) to increase. And since membrane 12 is shape-retaining, the imbibed water generates hydraulic pressure on the exterior of bag 14 causing bag 14 to be squeezed inwardly. This squeezing forces fluid 17 through tube 24 and out of the dispenser. Any air bubbles that were trapped within bag 14 during filling will tend to be located adjacent to the inner end of plug 15 or the inner surface of bag 14, depending on the attitude of the dispenser. Therefore, these air bubbles are not likely to block the entrance to tube 24 and interrupt or impede the flow of fluid 17 therethrough.

As indicated, fluid 17 may be an active agent composition. In such instances the dispensers 11 or 28 will, of course, discharge active agent directly. Alternatively, fluid 17 may be inert and the dispenser may be used simply as a displacement pump. In this alternative the dispenser will, of course, have to be suitably interconnected by well known means to a reservoir of the fluid (active agent) to be discharged, such that the inert fluid displaces the fluid from the reservoir in a predetermined regimen to the desired administration site. Such alternatives are particularly attractive in instances in which the fluid to be discharged is incompatible with bag 14.

EXAMPLES

The following examples are intended to further illustrate the above described dispensers and their manufacture. These examples are not intended to limit the invention in any way. Unless indicated otherwise, percentages and parts are by weight.

EXAMPLE 1

Cylindrical flexible bags (2.33 cm long, 3.81 mm I.D., and 4.67 mm O.D.) were injection molded at 180° C, 77–84 kg/cm$^2$ from an elastomeric styrene-butadiene copolymer (sold under the trade designation, Kraton 2104). A mandrel was inserted into each bag and mandrel supported bags were attached to a dipping platform.

A suspension of potassium sulfate particles in dioxane-cellulose acetate solution (50 wt %) was prepared and the mandrel supported bags were dipped into the suspension to a depth of 1.8 cm 4 times for 1 min. per dip with an intervening 15 min. room air drying period. This dipping coated the bags with an approximately 0.3 mm thick coating of the suspension.

A solution of cellulose acetate (sold under the trade designation, Eastman, E-398-10) in acetpme (15 wt %) was prepared and the mandrel-supported, potassium sulfate coated bags were dipped completely in the solution 20 times for 1 min. per dip with an intervening 15 min. drying period. Following this dipping the bags were oven dried at 60° C for 15 days. This dipping formed a cellulose acetate membrane approximately 0.65 mm thick about the entire bag exterior, including the potassium sulfate coated portion thereof.

Cylindrical plugs of the above described styrene-butadiene copolymer were injection molded. The plugs were 0.5 cm long, had a 3.9 mm O.D., and had a central axial bore 0.76 mm in diameter. The arcuate surfaces of the plugs were coated with a glue bead of a 20 wt % cyclohexane solution of the copolymer and the plugs were inserted into the open ends of the potassium sulfate-cellulose acetate coated bags. A 22 gauge needle was inserted through the bore of each plug and the plugged bags were placed in an oven at 60° C for 2 hr.

Flow moderators were prepared for each dispenser as follows. Head or cap members were injection molded from styrene-acrylonitrile copolymer. The heads were generally hemispherical, 6.6 mm in diameter with a 0.8 mm diameter diametrical bore. The arcuate surface of the heads had three equispaced grooves that intersected the bore. Twenty-one gauge needles were cut in 15 mm lengths, blunted, inserted into the heads and glued in place therein with an epoxy resin.

Example 2

Inner bags were made and coated with potassium sulfate as described in Example 1. Plugs for the potassium sulfate coated bags were made and glued into the open ends of the bags as in Example 1. The potassium sulfate coated, plugged bags were then completely coated with a 0.65 mm thick membrane of cellulose acetate in a small Wurster air suspension coater. (Air flow 15 m$^3$/min., air pressure 2 kg/cm$^2$, 5 wt % acetone solution of cellulose acetate, solution rate 50 ml/min., coating time 10 hr.) The bags were then oven dried at 60° C for 15 days and a hole was drilled in each membrane through to the plug bore. Flow moderators were made for each dispenser as in Example 1.

The dispensers of Examples 1 and 2 were tested in vitro and in vivo by filling them with various fluids via the plug bore, inserting the needle portion of the flow moderators through the plug bores down into the bags' interiors and placing the dispensers in an appropriate environment. In in vitro tests in water at 37° C using FD & C Blue No. 1 dye in water as the fluid charge the dispensers dispensed the solution at a flow rate of $1.7 \times 10^{-3}$ ml/hr with $\pm 1.3 \times 10^{-4}$ ml/hr deviation. In in vivo tests using the same fluid charge the dispensers were inserted subcutaneously into rats and provided a flow rate of $1.0 \times 10^{-3}$ ml/hr with $\pm 8 \times 10^{-5}$ ml/hr deviation.

Modifications of the above described dispensers that are obvious to those of skill in the mechanical, chemical, and other related arts are intended to be within the scope of the following claims.

We claim:

1. In an osmotically driven fluid dispenser comprising an inner flexible bag adapted to contain the fluid, an intermediate layer of an osmotically effective solute composition at least partly encapsulating the bag, an outer shape-retaining membrane encapsulating the layer of osmotically effective solute composition, said membrane being at least in part permeable to water, and a port that extends from the interior of the bag to the exterior of the dispenser through which the fluid may be charged into the bag and dispensed from the bag, the improvement comprising a conduit that is sized to fit snugly through the port and extending substantially into the interior of the bag after the fluid is charged into the bag.

2. The improvement of claim 1 wherein the bag is elongated and the conduit extends into the bag interior over at least about 50% of the elongated dimension thereof.

3. The improvement of claim 1 wherein the bag is elongated and the conduit extends into the bag interior over substantially the entire, but not all of, the elongated dimension thereof.

4. The improvement of claim 1 wherein the conduit is rigid.

5. The improvement of claim 1 wherein the length and inner diameter of the conduit are such as to prevent substantial diffusive flow of fluid therethrough.

6. The improvement of claim 1 wherein the exterior end of the conduit terminates in a blunt head.

7. The improvement of claim 6 wherein said head is shaped to fit snugly against the exterior of the dispenser and form a substantially smooth continuous surface therewith.

8. The improvement of claim 6 wherein the head has at least one groove in its exterior surface that communicates with the bore of the conduit to provide a flow channel for the fluid.

9. The improvement of claim 1 wherein the bag is elongated and the conduit is rigid, extends into the bag interior over substantially the entire, but not all of, the elongated dimension thereof, has a length and inner diameter such as to prevent substantial diffusive flow of fluid therefrom, and has a blunt head on its exterior end that is shaped to fit snugly against the exterior of the dispenser and form a substantially smooth continuous surface therewith and that has at least one groove in its exterior surface that communicates with the bore of the conduit to provide a flow channel for the fluid.

10. An osmotically driven fluid dispenser comprising an elongated flexible inner bag closed at one end and open at the other end and adapted to contain the fluid, a fluid tight plug fitted into the open end of the bag, a port in the plug that provides a passageway from the interior of the bag to the exterior of the dispenser through which the fluid may be charged into the bag, an intermediate layer of an osmotically effective solute composition partly covering the exterior of the bag such that a band of the bag exterior proximate to the open end of the bag is not covered by the layer, an outer shape-retaining semipermeable membrane covering the intermediate layer of osmotically effective solute composition and forming a fluid tight seal with the exterior of the bag at said band, and a conduit that is sized to fit snugly through the port and extending substantially into the interior of the bag after the fluid is charged to the bag to provide an outlet through which fluid may be dispensed from the bag under pressure.

11. The dispenser of claim 10 wherein the conduit extends into the bag interior over substantially the entire, but not all of, the elongated dimension thereof.

12. The dispenser of claim 11 wherein the conduit is rigid.

13. The dispenser of claim 10 wherein the length and inner diameter of the conduit are such as to prevent substantial diffusive flow of fluid therethrough.

14. The dispenser of claim 10 wherein the exterior end of the conduit terminates in a blunt head.

15. The dispenser of claim 14 wherein said head is shaped to fit snugly against the exterior of the dispenser and form a substantially smooth continuous surface therewith.

16. The dispenser of claim 14 wherein the head has at least one groove in its exterior surface that communicates with the bore of the conduit to provide a flow channel for the fluid.

17. The dispenser of claim 12 wherein the length and inner diameter of the conduit are such as to prevent substantial diffusive flow of fluid therethrough, and the exterior end of the conduit terminates in a blunt head that is shaped to fit snugly against the exterior of the dispenser and form a substantially smooth continuous surface therewith and that has at least one groove in its exterior surface that communicates with the bore of the conduit to provide a flow channel for the fluid.

* * * * *